(12) United States Patent
Caballero et al.

(10) Patent No.: US 8,956,599 B2
(45) Date of Patent: Feb. 17, 2015

(54) PHOSPHOROUS-CONTAINING SURFACTANTS AS POLYMERIC CATIONIC COMPOUND DEPOSITION AIDS

(75) Inventors: Eduardo Caballero, Bethlehem, PA (US); Abel G. Pereira, Bridgewater, NJ (US); Charles Moses, Stamford, CT (US); Robert Comber, Doylestown, PA (US)

(73) Assignee: Croda, Inc., Edison, NJ (US)

( * ) Notice: Subject to any disclaimer, the term of this patent is extended or adjusted under 35 U.S.C. 154(b) by 0 days.

(21) Appl. No.: 13/226,003

(22) Filed: Sep. 6, 2011

(65) Prior Publication Data

US 2011/0318294 A1  Dec. 29, 2011

Related U.S. Application Data

(63) Continuation of application No. 12/220,672, filed on Jul. 25, 2008, now abandoned.

(60) Provisional application No. 60/962,213, filed on Jul. 27, 2007.

(51) Int. Cl.

| A61K 8/73 | (2006.01) |
|---|---|
| D06P 5/02 | (2006.01) |
| A61K 8/55 | (2006.01) |
| A61K 8/81 | (2006.01) |
| A61Q 5/00 | (2006.01) |
| A61Q 5/10 | (2006.01) |
| A61Q 5/12 | (2006.01) |

(52) U.S. Cl.
CPC . *A61K 8/731* (2013.01); *A61K 8/55* (2013.01); *A61K 8/556* (2013.01); *A61K 8/817* (2013.01); *A61Q 5/004* (2013.01); *A61Q 5/10* (2013.01); *A61Q 5/12* (2013.01); *A61K 2800/5426* (2013.01)
USPC ........................................... 424/70.17; 8/442

(58) Field of Classification Search
None
See application file for complete search history.

(56) References Cited

U.S. PATENT DOCUMENTS

| 6,117,915 | A | * | 9/2000 | Pereira et al. ................... 516/57 |
| 2002/0037267 | A1 | * | 3/2002 | Guillou et al. ............. 424/70.23 |
| 2002/0197231 | A1 | | 12/2002 | L'Alloret et al. |

FOREIGN PATENT DOCUMENTS

| EP | 0400976 | A1 | | 12/1990 | |
| EP | 1484047 | A1 | * | 12/2004 | ............... A61K 7/13 |
| JP | 03-068509 | A | | 3/1991 | |
| JP | 2002087950 | A | | 3/2002 | |
| JP | 2002356418 | A | | 12/2002 | |
| JP | 2003522726 | A | | 7/2003 | |
| JP | 2006526655 | A | | 11/2006 | |
| WO | 9955295 | A1 | | 11/1999 | |
| WO | 2004108102 | A1 | | 12/2004 | |

OTHER PUBLICATIONS

Japanese Office Action for Application No. 2010-518241 dared Jul. 23, 2013.

* cited by examiner

*Primary Examiner* — Michael B Pallay
(74) *Attorney, Agent, or Firm* — Lerner, David, Littenberg, Krumholz & Mentlik, LLP

(57) ABSTRACT

Personal care products exhibiting superior conditioning and/or color fastness can be obtained by use of mixtures of certain phosphate esters and polyquats.

18 Claims, 4 Drawing Sheets

US 8,956,599 B2

PHOSPHOROUS-CONTAINING SURFACTANTS AS POLYMERIC CATIONIC COMPOUND DEPOSITION AIDS

CROSS-REFERENCE TO RELATED APPLICATIONS

This application is a continuation, of U.S. application Ser. No. 12/220,672, filed on Jul. 25, 2008, which claims the benefit of the filing date of U.S. Provisional Patent Application No. 60/962,213 filed Jul. 27, 2007, the disclosures of which are incorporated herein by reference.

BACKGROUND OF THE INVENTION

The invention relates to phosphorous-containing emulsifiers as polyquaternium compound deposition aids, which enhance and independently impart conditioning properties onto a substrate, more particularly to hair and skin.

Phosphate esters of alkoxylated fatty alcohols, such as those disclosed in U.S. Pat. No. 3,963,628 to Park and U.S. Pat. No. 4,369,134 to Deguchi et al., are described as emulsifiers for oil-in-water emulsions. U.S. Pat. No. 6,117,915, assigned to Croda, Inc., the assignee of the present application, discloses, inter alia, a mixture of mono- and di-phosphate esters of alkoxylated and nonalkoxylated fatty alcohols. These materials are described as being superior emulsifiers, and may be mixed with other conventional ingredients including, as a detergent, quaternium-26.

U.S. Pat. No. 4,381,259 discloses, also as an emulsifier, a mixture of mono- and di-alkoxylated phosphate esters of fatty alcohols generally ranging from $C_8$ to $C_{18}$, alkoxylated with ethylene oxide and propylene oxide. These may be combined with, inter alia, a quaternized guar gum. U.S. Pat. No. 4,298,494 contains a similar disclosure of a mixture of mono- and di-ethoxylated phosphate esters of various fatty alcohols. These may be mixed with polygalactomannan gum. Finally, U.S. Pat. No. 5,683,683 describes a mixture of nonfatty alcohol based quaternized phosphate esters and polyquaternium or guar hydroxypropyltrimonium chloride. These materials are all described as being useful in conditioning formulations.

There is no indication in these prior art references that a mixed alkoxylated and nonalkoxylated phosphate esters can be used to aid deposition of polycationic compounds to enhance and independently impact conditioning properties or that any combination of phosphate esters and polycationic compounds can provide particularly beneficial results.

SUMMARY OF THE INVENTION

The present invention is directed to formulations, compositions, or personal care products comprising a polyquaternium compound ("polyquat"), a phosphate ester, and an additional ingredient. The phosphate esters can be alkoxylated or nonalkoxylated esters of fatty alcohols, but at least some of the phosphate esters are nonalkoxylated. In some embodiments, only nonalkoxylated phosphate esters are used. In other embodiments, mixtures of nonalkoxylated and alkoxylated phosphate esters are used. In either case, the alkoxylated and/or nonalkoxylated phosphate esters may comprise mono- and/or diphosphate esters, which may be present in any proportion relative to each other.

One embodiment of the invention is a personal care product comprising at least one polyquat having greater than 4 quaternary nitrogens in its structure and having the weight average molecular weight of between about 4000 and about 2,000,000. Also included in this embodiment is at least one nonalkoxylated phosphate ester comprising a fatty alcohol based group of a chain length of between about $C_8$ and about $C_{22}$, which may be linear, branched, saturated or unsaturated and/or substituted or unsubstituted. In certain aspects of this embodiment, the phosphate esters used may also include alkoxylated phosphate esters.

In another embodiment is a personal care product comprising at least one polyquaternium compound having greater than 4 quaternary nitrogens in its structure and having a weight average molecular weight of between about 4,000 and 2,000,000. Also included in this embodiment is a mixture of alkoxylated and nonalkoxylated phosphate esters of fatty alcohols wherein the phosphate esters have a fatty alcohol based group having a chain length of between about 8 and 22 carbon atoms, wherein these alkoxy groups comprise ethylene oxide, propylene oxide, derivatives of these oxides, or mixtures thereof. About 1 to 50 moles of an alkylene oxide are used per mole of fatty alcohol based group. The alkoxylated and nonalkoxylated phosphate esters are generally present in an amount such that no more than about 60% by weight of the phosphate esters are alkoxylated and wherein the alkoxylated and the nonalkoxylated phosphate esters comprise both mono- and diphosphate esters. Typically, the amount of diphosphate esters in this embodiment is at least about 40% by weight of the total amount of the phosphate esters. Moreover, the ratio of the phosphate ester to the polyquaternium compound is about 1.5:1 to about 100:1; and wherein a total amount of the phosphate esters and the polyquaternium compounds combined ranges from between about 0.20% to about 15% by weight of the personal care product. This embodiment also includes an additional ingredient, and in some embodiments multiple additional ingredients.

In another embodiment, personal care products are contemplated which comprises a polyquat having 100 or more quaternary nitrogen groups and having a weight average molecular weight of between about 30,000 and about 1,000,000 and at least some nonalkoxylated phosphate esters of fatty alcohols.

In yet another embodiment is a personal care product comprising a polyquaternium compound having 100 or more quaternary nitrogen groups and having a weight average molecular weight of between about 30,000 and about 1,000,000 and further comprising at least some nonalkoxylated phosphate esters of fatty alcohols wherein the phosphate esters have a fatty alcohol based group having a chain length of between about 12 and 18 carbons. Generally, the ratio of the phosphate esters to the polyquaternium compounds is 2:1 or greater. Moreover, the total amount of the phosphate esters and the polyquaternium compounds range from between about 0.5% to about 5% by weight of the personal care product. This embodiment also includes an additional ingredient.

In some embodiments, the present invention relates to personal care products selected from the group consisting of a shampoo, conditioner, body wash, cleanser, hair color and hair relaxer.

In other embodiments, the present invention relates to a personal care product selected from the group consisting of a shampoo, conditioner, conditioning shampoos and hair colors specifically intended for treatment of color treated hair, also referred to herein as synthetically colored hair.

In yet other embodiments, these personal care products are selected from the group consisting of a shampoo, conditioner, conditioning shampoo, a shampoo and/or conditioner used in connection with synthetically colored hair, body wash, cleanser, skin care product or hair color.

In one embodiment, the present invention relates to a hair relaxer composition wherein, if the phosphate ester is a mixture of dicetyl phosphate and ceteth-10 phosphate, the polyquat is not Polyquaternium-6; and if the polyquat is Polyquaternium-6, the phosphate ester is not a mixture of dicetyl phosphate and ceteth-10 phosphate.

It has been found, unexpectedly, that personal care products comprising at least one polyquaternium compound and at least one nonalkoxylated fatty alcohol phosphate ester impart superior conditioning as compared to the prior art.

A series of tests were run on materials similar to those described in some of the prior art patents discussed above. The results of such tests were expressed in terms of conditioning power, as measured by wet combing strength. While some materials modestly increased wet combing strength, others decreased it. None, however, provided a great improvement in performance over the use of water alone. Nor did any provide the superior properties observed with the formulations of the present invention.

Superior conditioning can be quantified as a reduction in total work, as measured in terms of wet combing force. "Accordingly, superior conditioning" means a reduction in total work of at least about 10 Joules when compared to hair treated only with water. In some instances, a reduction of at least 20 Joules (change in total work) relative to water is realized.

Some of these personal care products of the present invention exhibit not only exhibit superiority when compared to identical products using only the polyquats or the phosphate esters disclosed, but also when compared to mixtures of alkoxylated fatty alcohol phosphate esters and polyquats, as well as non-fatty alcohol based quaternized phosphate esters and a polyquat like those described in the prior art.

In some embodiments, the personal care products of the present invention provide superior color fastness. "Superior color fastness" means that repeated shampooing and/or conditioning will strip out or reduce the degree of color in colored hair to a lesser degree than the product without the combinations of polyquats and phosphate esters of the invention.

In still another embodiment, some of the personal care products of the present invention are designed to be used in connection with colored hair to improve color fastness (to preserve the degree of hair color in synthetically colored hair) while also providing superior conditioning. These personal care products include shampoos, conditioners, conditioning shampoos, hair colors and the like.

DETAILED DESCRIPTION

Figure 1:
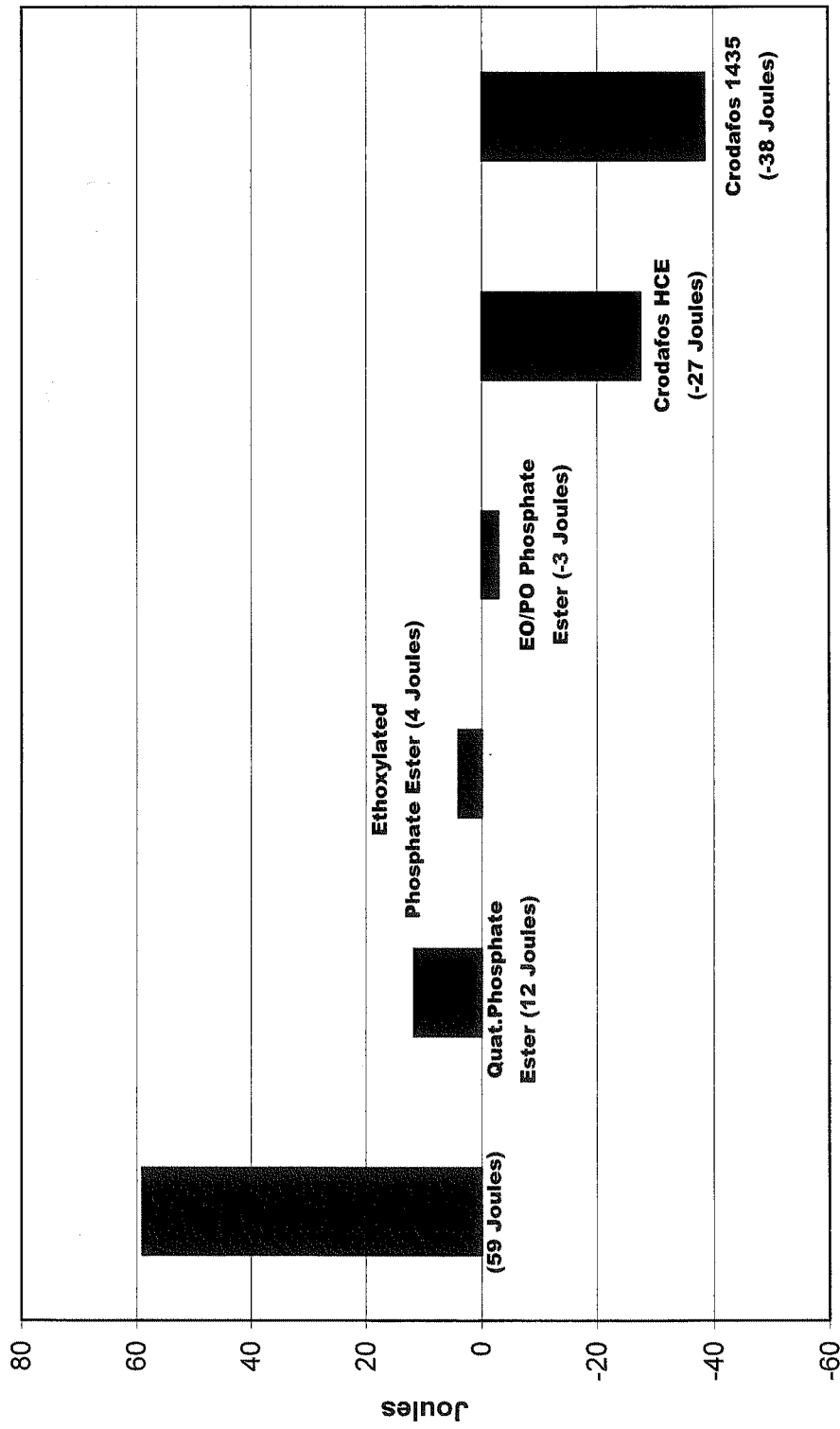
FIG. 1 is a graph depicting the combing forces measured after treating medium European brown virgin hair tresses with the formulations in Examples 1 and 2.

The present invention is directed to compositions and personal care products exhibiting superior conditioning and/or color fastness through the use of mixtures of certain phosphate esters and polyquaternium compounds (also referred to as "polyquats"). More specifically, the present invention is directed to a mixture of polyquaternium compounds and phosphate esters of fatty alcohol groups, where the fatty alcohol groups of the phosphate esters may be nonalkoxylated or may be mixtures of nonalkoxylated and alkoxylated fatty alcohol groups (referred to herein as "phosphate esters"). The polyquat(s) and phosphate ester components, additional ingredients, and compositions, formulations and personal care products comprising the same are enumerated herein.

DEFINITIONS AND TERMINOLOGY

All percentages and ratios used herein are by weight of the total composition and all measurements made are at about room temperature and normal pressure unless otherwise designated. "Room temperature" as defined herein means a temperature ranging between 22° C. and 26° C. All temperatures are in degrees Celsius unless specified otherwise.

The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise.

As used herein, "consisting essentially of" means that the invention may include ingredients in addition to those recited in the claim, but only if the additional ingredients do not materially alter the basic and novel characteristics of the claimed invention. Preferably, such additional ingredients will not be present at all or only in trace amounts. However, it may be possible to include up to about 10% by weight of materials that could materially alter the basic and novel characteristics of the invention as long as the utility of the compounds (as opposed to the degree of utility) is maintained.

All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

It will be appreciated that, when discussing the amounts of the phosphate esters and polyquats useful in accordance with the present invention, the amounts recited refer to the dry weight of the phosphate ester or polyquat compounds respectively, not counting any carrier, solvents or diluents. For example, CRODAFOS-CES is a material available from applicant which contains about 25% by weight of phosphate esters and about 75% by weight of fatty alcohol. The amount of fatty alcohol solvent would not be considered in determining the amount of phosphate ester in such a composition. In another example, OPTASENSE-CP6 is a polyquaternary material available from Croda, Inc. This material ranges from 39% to 41% by weight of a polyquaternary compound, Polyquaternium-6 (about 40%), with the balance being solvent or carrier. Accordingly, in determining the amount of polyquat in a final product, the amount of solvent or carrier will not be considered. Of course, this material could also be characterized as having a specific cationic activity.

Note that while the specification and claims may refer to a final product or personal care product such as, for example, a shampoo or conditioner as containing a certain reactant or a certain amount of, for example, a specific polyquat, it may be difficult to tell from the product that any particular recitation is satisfied. Such a recitation may be satisfied, however, if the materials used prior to final production, for example, meet that recitation. Indeed, as to any property or characteristic of a final product which cannot be ascertained from the final product directly, it is sufficient if that property resides in the components recited just prior to production steps used to make the personal care product.

Croda hereby incorporates by reference U.S. Pat. No. 6,117,915 to Pereira et al., which issued on Sep. 12, 2000 to Croda, Inc. of Parsippany, N.J., for its disclosure of mixed fatty alcohol phosphate esters and methods of manufacturing same.

believed that while the predominant fraction will contain 10 alkoxy groups, other fractions will contain less than 10 molecules of ethylene oxide per phosphate ester molecule. In any event, however, a reference to a PEG 10 cetyl alcohol or a cetyl alcohol made with 10 moles of ethylene oxide refers to the reaction product of those two materials in those amounts.

As another example, Table 1 shows known approximate weight percentages of some of the $C^{20}+$ components in some of the common oils that can be used as a source of fatty alcohols used to produce alkoxylated and/or nonalkoxylated phosphate esters of the invention:

TABLE 1

| Substance | $C^{20}:0$ | $C^{20}:1$ | $C^{20}:4$ | $C^{20}:5$ | $C^{22}:0$ | $C^{22}:1$ | $C^{22}:5$ | $C^{22}:6$ | $C^{24}:0$ |
|---|---|---|---|---|---|---|---|---|---|
| Cod liver oil | 8.8-14.6% | | | 2.6-9% | | 4.6-13.3% | 1-2% | 8.6-19% | |
| Herring oil | | 1.5-19.2% | | 4.6-10.2% | | 2.8-19.9% | 1-3.7% | 3.8-24.1% | |
| Menhaden oil | | 0.9-2.7% | 0.6-1.2% | 10.2-13.5% | | 0.7-1.7% | 1.1-2.3% | 3.3-14% | |
| Pilchard (Sardine) oil | | 3.2% | 1.6% | 16.9% | | 3.6% | 2.5% | 12.9% | |
| HEAR oil | | 0.8-13.5% | | | | 20.1-59.4% | | | 0.1-1.4% |
| Mustard Seed oil | | 7% | | | | 44.2% | | | |

Phosphate Esters

Turning first to the phosphate esters, it will be appreciated that phosphate esters or mixtures thereof can be complex depending on a number of factors including their origin (such as the feedstocks used to produce the fatty alcohols and the methods used to produce these feedstock materials).

Therefore, when something is referred to as being, containing, or being made from, for example, a cetyl alcohol group, that means that the predominant fraction (most abundant compared to the amount of any other fatty alcohol in the feedstock) of the fatty alcohols used to produce the phosphate esters in accordance with the present invention are derived from $C_{16}$ based fatty alcohols. However, there may be many other fatty alcohol groups of varying chain lengths present in the raw material or feedstock which may be converted into phosphate esters along with the $C_{16}$ species. The resulting mixture is still used in accordance herewith and would be identified as a cetyl containing material or a $C_{16}$ material. Feedstocks can also be oils containing glycerides of fatty acids from which the fatty alcohols can be derived. Here too, the relative abundance would still apply.

Similarly, if reference is made to a range of chain lengths such as, for example, $C_8$-$C_{22}$, it means that the predominant fraction of the fatty alcohols used to produce the phosphate esters would fall within that range of chain lengths. However, longer and shorter chain length materials may also be present and would be converted into the respective phosphate esters and used in accordance with the present invention.

When alkoxylated fatty alcohols are used, the fatty alcohol may be characterized as, for example, being a "PEG 10" or may be characterized as containing 10 moles of ethylene oxide. These two types of terms are used synonymously. It will be appreciated that this means that while roughly 10 moles of ethylene oxide may have been added to the reaction mixture per mole of fatty alcohol, not all of the resulting alkoxylated phosphate esters will include exactly 10 molecules of ethylene oxide per phosphate ester molecule. It is Accordingly, behenyl alcohol can be derived from rapeseed oil, especially high erucic rapeseed oil (HEAR oil), which typically contains 46% of $C^{22}:1$ alkyl (erucic), 1.5% of $C^{22}:0$ alkyl (behenic), and 11% of $C^{22}:1$ alkyl (gadoleic) by weight. The HEAR oil can be hydrogenated to yield a composition containing about 48% $C^{22}:0$ alkyl (behenic) which can further be distilled to yield any desired higher concentrations of $C^{22}:0$ alkyl (behenic) acids which are then further converted to fatty alcohols. Alkoxylated and/or nonalkoxylated phosphate esters can be produced from these hydrogenated rapeseed oil derived alcohols or any glyceride. Other oils that can include fatty acid containing glycerides that can be converted into fatty alcohols include, without limitation, palm oil (predominant fractions are palmitic and/or oleic fatty acids), coconut oil (lauric ($C_{12}$) fatty acids are the predominant fraction), corn oil, cottonseed oil, olive oil, peanut oil, sesame oil, palm kermal oil, safflower oil, sunflower oil, soybean oil and the like. Of course, any source of fatty alcohols falling within the scope of the invention are contemplated.

Nonalkoxylated Phosphate Esters

In some embodiments, at least some of the phosphate esters mixed with the polyquats are nonalkoxylated. In other embodiments, only nonalkoxylated phosphate esters are mixed with the polyquats.

In some embodiments, the phosphate esters are created from phosphate groups and fatty alcohol groups of a chain length having $C_8$ to $C_{22}$. In other embodiments, the phosphate esters are created from phosphate groups and fatty alcohol groups having a chain length of $C_{12}$ to $C_{22}$. In yet other embodiments, the phosphate esters are created from phosphate groups and fatty alcohol groups having a chain length of $C_{12}$ to $C_{18}$. The fatty alcohol derived groups may be saturated or unsaturated, linear or branched and/or substituted or unsubstituted and may be of any origin as discussed previously.

In some embodiments, the nonalkoxylated phosphate esters of the invention do not include a quaternary nitrogen. In other embodiments, the nonalkoxylated phosphate esters include a quaternary nitrogen. In yet other embodiments, the phosphate esters are liquid or flowable at room temperature.

Generally, the phosphate group is derived from phosphorylating agents known to those skilled in the art. Such agents include, without limitation, phosphorous pentoxide, and polyphosphoric acid.

In some embodiments, it is possible, and indeed desirable, that the nonalkoxylated phosphate esters used be a mixture of monophosphate esters and diphosphate esters (indeed, any proportion of these may be used). In other embodiments, at least about 10% by weight of the nonalkoxylated phosphate esters will be diphosphate esters with the balance being monophosphate esters.

In yet other embodiments, at least about 40% by weight of the nonalkoxylated fatty esters are diphosphate esters. In a further embodiment, the nonalkoxylated fatty esters comprise more than about 50% by weight of diphosphate esters (i.e. a majority of the nonalkoxylated phosphate esters are diphosphate esters).

Examples of nonalkoxylated monophosphate esters (which may contain some amount of diphosphate ester(s)) include monocetyl phosphate esters, commercially available from DSM Nutritional Products, 616 Dayton Ave., Ames, Iowa 50010; Colonial Chemical Inc., 225 Colonial Drive, South Pittsburgh, Tenn. 37380; Croda Chemicals, Cowick Hall Sanith Goole East Yorkshire NA14 9 AA England; and Clariant, 4000 Monroe Road, Charlotte, N.C., 28205; under the trade names Amphisol A, Colafax CPE, Crodafos MCA, Hostaphat CC100, respectively; monocetyl phosphate ester is also available in mixtures such as Crodafox CP (Croda, Inc.) and Stepan CP3 (Stepan), 22 W. Frontage Road, Northfield, Ill. 60093. Other nonalkoxylated phosphate esters include dioleyl phosphate and isostearyl phosphate.

Diphosphate esters (also mixtures of diphosphate and monophosphate esters, but rich in diphosphate esters) can be made in accordance with U.S. Pat. No. 6,117,915, and in particular, Example 1 thereof.

Mixtures of Nonalkoxylated and Alkoxylated Phosphate Esters

In some embodiments, a mixture of nonalkoxylated and alkoxylated phosphate esters may be used in conjunction with the polyquats (i.e. at least some of the phosphate esters are alkoxylated).

In some embodiments, the mixture contains the nonalkoxylated phosphate esters described herein mixed with a blend of mono- and di-ester phosphates of alkoxylated fatty alcohols containing between about 8 to about 22 carbon atoms and alkoxylated with between about 1 and about 50 moles of an alkylene oxide. In other embodiments, the amount of alkoxylation ranges from between about 1 mole to about 30 moles for the alkoxylated phosphate esters. In yet other embodiments, the amount of alkoxylation ranges from between about 3 moles to about 25 moles for the alkoxylated phosphate esters.

In some embodiments, the mixture of nonalkoxylated and alkoxylated phosphate esters used each have a chain length of $C_{12}$ to $C_{18}$, wherein the alkoxylated materials have between about 3 and about 15 moles of alkoxy groups.

The alkylene oxide used to create the alkoxylated phosphate ester can be ethylene oxide, propylene oxide, derivatives of these oxides, or mixtures thereof. Accordingly, the resulting alkoxy groups are ethoxy, propoxy, derivatives of these, or mixtures of both.

The mono- and di-ester ratio for the alkoxylated phosphate esters is the same as previously described for nonalkoxylated phosphate esters. Accordingly, in some embodiments, at least about 10% by weight of the alkoxylated phosphate esters will be diphosphate esters with the balance being monophosphate esters. In other embodiments, at least about 40% by weight of the alkoxylated fatty esters are diphosphate esters. In yet other embodiments, the alkoxylated fatty esters comprise 50% or more by weight of diphosphate esters (i.e. a majority of the alkoxylated phosphate esters are diphosphate esters).

The mono- and di-ester ratio in the nonalkoxylated phosphate esters used in the mixtures is the same as previously described.

There is no requirement that the ratio of mono- to diphosphate esters in the nonalkoxylated phosphate esters be the same as that in the alkoxylated phosphate esters, although the same or similar proportions are contemplated. For example, the mono- to di-ester ratio can be 9:1 for the alkoxylated species while the ratio for the non-alkoxylated species is 1:4. In some embodiments, however, the total amount of diphosphate esters of both alkoxylated and nonalkoxylated phosphate esters combined is equal to or greater than the amount of monophosphate esters. Nor is it required that the fatty alcohol species of the alkoxylated and nonalkoxylated phosphate esters have the same chain lengths, degree of saturation, substitution, or the like. Indeed, any combination of nonalkoxylated and alkoxylated phosphate esters may be used provided they meet the requirements of the present invention.

In some embodiments, when a mixture of alkoxylated and nonalkoxylated phosphate esters are used, the amount of alkoxylated phosphate esters should not exceed about 80% by weight relative to the total amount of phosphate esters. In other embodiments, when a mixture of alkoxylated and non-alkoxylated phosphate esters are used, the amount of alkoxylated phosphate esters should not exceed about 60% by weight relative to the total amount of phosphate esters. In yet other embodiments, when a mixture of alkoxylated and non-alkoxylated phosphate esters are used, the amount of alkoxylated phosphate esters should not exceed about 50% by weight relative to the total amount of phosphate esters (i.e. the amount of nonalkoxylated phosphate esters is about equal to or greater than the amount of alkoxylated phosphate esters present). In further embodiments the amount of diphosphate esters relative to the amount of monophosphate esters is at least about 40% by weight of the total amount of said phosphate esters. Indeed, as stated herein, all of the phosphate esters could be nonalkoxylated.

Mixtures of alkoxylated and nonalkoxylated phosphate esters which are useful are described and claimed in U.S. Pat. No. 6,117,915 (hereinafter the '915 patent). In one illustration, a nonalkoxylated lauryl phosphate may be produced as described in Example 1 of the '915 patent. Generally, a 2000 mL four-necked round-bottom flask is charged with 131.6 g (3.0 moles) of lauryl alcohol. The material is heated to 65° C. and 236 g (1.0 mole) of phosphorous pentoxide ($P_2O_5$) is added with stirring. The mixture is allowed to react for four hours. The final product is cooled and recovered as lauryl phosphate having an acid value of 234 mg KOH, a diester content of 50.1% and a monoester content of 39.8%.

An alkoxylated phosphate ester using 5 moles of ethylene oxide per mole of behenyl alcohol can be made as described in Example 2 of the '915 patent. Specifically, ethylene oxide is bubbled into 596.8 g of behenyl alcohol in the presence of potassium hydroxide catalyst until five moles of ethylene oxide are added per mole of behenyl alcohol. An off-white solid (PEG-5 behenyl alcohol ether) is the major product. A four-necked flask is charged with 920.26 g (3.0 moles) of the PEG-5 behenyl ether and the material is heated to 65° C., followed by the addition of 78.9 g of $P_2O_5$, with stirring. The reaction mixture is allowed to stir for four hours. The final product is recovered as PEG-5 behenyl phosphate having an acid value of 126.5 mg KOH, a diester content of 61% and a monoester content of 37.4%.

A mixed system of these alkoxylated and nonalkoxylated phosphate esters can be created, for example, by stirring 60% w/w of the PEG-5 behenyl phosphate and 40% w/w of the lauryl phosphate. The vessel contents are heated, such as to 70° C., and allowed to mix for 30 minutes, and then recovered as a mixture of mono- and diester phosphates of PEG-5 behenyl alcohol and lauryl alcohol having an acid value of 169.5 mg KOH. See Example 3 of the '915 patent.

The fatty alcohols and phosphates used to create the nonalkoxylated phosphate esters described previously may all be used to produce the alkoxylated phosphate esters useful in accordance with the invention. It will be appreciated that in a particularly preferred embodiment, neither the alkoxylated nor the nonalkoxylated phosphate esters include a quaternary nitrogen group.

Particularly preferred alkoxylated phosphate esters in accordance with the present invention include PEG 10 cetyl alcohol, PEG 5 oleyl and PEG 10 isostearyl phosphate esters.

Particularly preferred mixtures of nonalkoxylated and alkoxylated phosphate esters that may be used in accordance with the present invention include CRODAFOS CES, available from Croda, Inc., which is a mixture of PEG 10 cetyl alcohol phosphate esters (about 10% w/w) plus phosphate esters of cetyl alcohol (about 15% w/w), which is a mixture of $C_{16}$ chain length fatty alcohols which are saturated and linear mixed in about 75% w/w cetearyl alcohol as a carrier; CRODAFOS HCE, which is a PEG 5 oleyl phosphate ester (about 55% w/w) with a nonalkoxylated di-oleyl phosphate ester (about 45% w/w) which is a mixture of unsaturated fatty alcohol groups having carbons in length and CRODAFOS 1435, which is a PEG 10 isostearyl phosphate ester (about 55% w/w) with a nonalkoxylated di-isostearyl phosphate ester (about 45% w/w) which is a mixture of $C_{18}$ fatty alcohol based groups which are mostly saturated and branched. Also useful is CRODAFOS CS20 ACID, which consists of ceteth-20-phosphate (about 30% w/w) (and) dicetylphosphate (about 20% w/w) in cetearyl alcohol as a carrier. In each case, there is the presence of some nonalkoxylated phosphate ester for improved performance.

Amounts of Phosphate Esters in Products

In some embodiments, the total amount of phosphate esters useful in personal care products or other compositions or formulations ranges from about 0.15% to about 10% relative to the total weight of the product, composition, or formulation. In other embodiments, the total amount of phosphate esters useful in personal care or other compositions or formulations products ranges from about 0.2% to about 10% relative to the total weight of the product, composition, or formulation. In yet other embodiments, the total amount of phosphate esters useful in personal care products or other compositions or formulations ranges from about 0.5% to about 5% relative to the total weight of the product, composition, or formulation.

Polyquaternary Compounds

The personal care products of the current invention also include at least one polyquaternium compound. Polyquaternary compounds in accordance with the present invention contain greater than four quaternary nitrogens in their structure per molecule.

Generally, these molecules have a weight average molecular weight ranging from about 4,000 to about 10 million; although, in some instances they may be greater. See, for example, U.S. Pat. No. 6,544,500 to O'Toole et al., issued on Apr. 8, 2003 and assigned to the Procter & Gamble Co. and in particular, the discussion of cationic conditioning components described at column 11, line 35 through column 12, line 34, which is hereby incorporated by reference.

In some embodiments, the polyquats hereof have a weight average molecular weight which is at least about 4,000, typically at least about 10,000, and less than about 10 million, preferably about 2 million or less, and more preferably about 1 million or less.

In other embodiments, the molecular weight of the polyquats ranges from about 100,000 to about 2 million. In yet other embodiments, the molecular weight of the polyquats ranges from about 4,000 to about 2,000,000. In yet further embodiments, the molecular weight is from about 30,000 to about 1,000,000.

While polyquats may be recited as having a particular number of quaternary nitrogen groups (also referred to as "quat content") or having a specific molecular weight, or even a specific composition, it will be appreciated that, as in most organic reactions, variations, side products and co-reactants may and will occur in various and often unpredictable proportions. The final qualities of these materials shall be judged sufficient if they may be sold commercially bearing the designations that are common to them. Therefore, for example, Polyquaternium-6 may contain a distribution of materials of varying molecular weight and quat content, however, if it would be legitimate to sell it under the name Polyquaternium-6, it qualifies. Similarly, if the predominant fraction of the polyquat (largest single fraction) meets the recitations of this application and/or claims, they are satisfied.

The polyquats will generally have cationic nitrogen-containing moieties such as quaternary ammonium or cationic amino moieties, and mixtures thereof. In some embodiments, the cationic charge density will be preferably at least about 0.05 meq/g, more preferably at least about 0.5 meq/g, even more preferably at least about 1.1 meq/g, most preferably at least about 1.2 meq/g. Generally, for practical purposes, the polyquats will have a cationic charge density of less than about 7 meq/g, preferably less than about 5 meq/g, more preferably less than about 3.5 meq/g, even more preferably less than about 2.5 meq/g.

Cationic charge density of the cationic polymer can be determined using the Kjeldahl Method (U.S. Pharmacopoeia—Chemical tests—<461> Nitrogen Determination—method II). Those skilled in the art will recognize that the charge density of amino-containing polymers may vary depending upon pH and the isoelectric point of the amino groups. The charge density should be within the above limits at the pH of intended use. Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used as this list is not exclusive.

In some embodiments, the nitrogen containing polyquats include at least about 100 quaternary nitrogens and preferably several hundred. Their weight average molecular weight preferably ranges from between about 30,000 and about 1 million. While there is no maximum amount, the ratios of materials and the overall amounts described herein must still be met.

These polyquats can be synthetic or natural. By natural, it is meant that the polyquats are derived from natural materials. Polyquats may include polymers based on acrylamide and/or dimethyl allylamonium chloride such as Polyquaternium 6, Polyquaternium 7 and the like. Polymeric quaternium ammonium salt of Guar gum such as Guar Hydroxypropyltrimonium chloride and the like are also contemplated. Polymeric quaternium ammonium salts of cellulose such as Polyquaternium 10 and the like are also contemplated. Polymeric quaternium ammonium salts of starch are also contemplated. Polyquaterniums listed on the CTFA dictionary that meet the criteria set forth herein may be used. More particularly, in preferred embodiments, the polyquats are selected from the group consisting of, without limitation, Polyquaternium-4, Polyquaternium-5, Polyquaternium-6, Polyquaternium-7, Polyquaternium-10, Polyquaternium-11, Polyquaternium-15, Polyquaternium-16, Polyquaternium-22, Polyquaternium-24, Polyquaternium-28, Polyquaternium-0, Polyquaternium-31, Polyquaternium-32, Polyquaternium-34, Polyquaternium-35, Polyquaternium-36, Polyquaternium-37, Polyquaternium-39, Polyquaternium-43, Polyquaternium-44, Polyquaternium-45, Polyquaternium-47, Polyquaternium-48, Polyquaternium-49, Polyquaternium-50, Polyquaternium-52, Polyquaternium-53, Polyquaternium-54, Polyquaternium-56, Polyquaternium-57, Polyquaternium-58, Polyquaternium-60, Polyquaternium-63, Polyquaternium-64, Polyquaternium-65, and Guar Hydroxypropyltrimonium Chloride.

In accordance with the present invention, the minimum amount of polyquat material present in the personal care products of the present invention is at least about 0.1%, or more preferably at least about 0.3% relative to the total weight of the product. Although there is no maximum amount, the ratios of materials and the overall amounts described herein must still be met.

In some embodiments, when used in personal care products, the ratio of the phosphate esters to the polyquats will be at least about 1.5:1. In other embodiments, this ratio is at least about 2:1. In yet other embodiments, this ratio is more about 4:1 or greater. Ratios up to about 100:1 are possible. This is based on the weights of the relative materials not including solvents, carriers or diluents. Thus, the amount of phosphate esters present generally exceeds the amount of polyquats used by weight.

The total amount of both (phosphate esters and polyquats) used in personal care products in accordance with the present invention will vary with a number of factors including the type of product to be used, the other ingredients (see e.g. the "additional ingredients" below) that will make up the final product and the like.

Generally, the total amount of polyquat and phosphate ester will be no less than about 0.20% and no more than about 15% relative to the total weight of the final formulation; preferably at least about 0.20% and no more than about 10%; and more preferably in the range of about 0.5% to about 5% relative to the total weight of the final formulation. When shampoos, conditioners, body washes and the like are produced, that range is about 0.50% to about 3% by weight. For hair color, generally the amounts used may range to a higher amount generally ranging from between about 1% to about 5% by weight.

In some embodiments, the polyquats utilized have a weight average molecular weight ranging from between about 30,000 to about 1,000,000 with at least 100 quaternary nitrogen groups per molecule. Moreover, in these embodiments, there would be a mixture of alkoxylated and nonalkoxylated phosphate esters and they would be present in a ratio of 4:1 or greater for most personal care products, and 2:1 or greater for a hair color. These may be used in any conventional product or can be the platform upon which new personal care products are based. They represent excellent conditioners and provide superior conditioning even over mixtures of other similar ingredients.

Formulations

Figure 4:
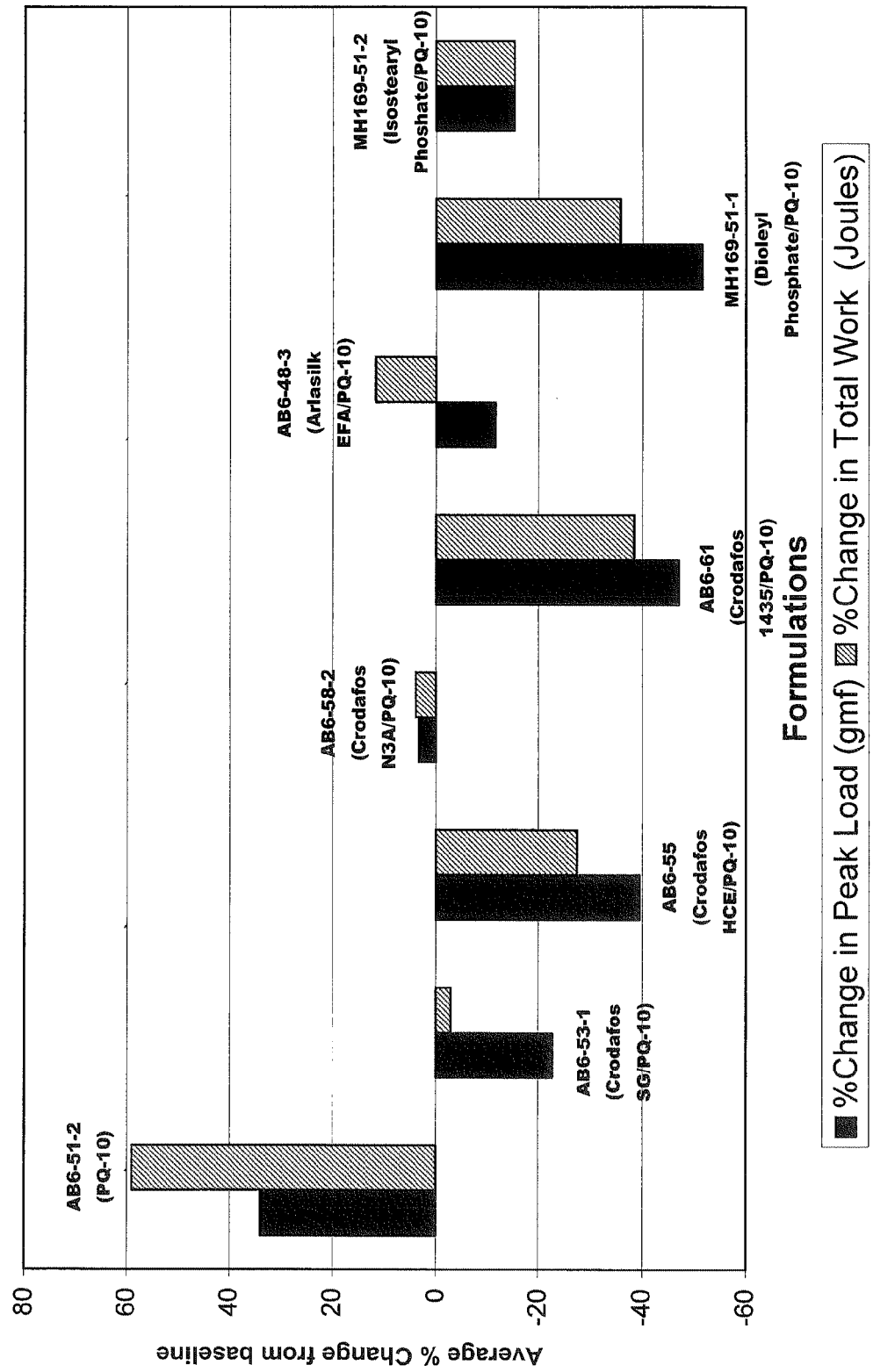
FIG. 4 is a graph depicting the combing forces measured (peak load and total work) after treating hair tresses with the formulations of Examples 1 and 2.

As shown in FIGS. 1 and 4, the personal care products of the invention have superior conditioning properties when compared to formulations similar to those found in the art. As explained in Examples 1 and 2, the control formulation was prepared by using Polyquaternium compound alone, i.e., Polyquaternium-10 ("PQ-10") without a phosphate ester. The other formulations included both the quats and phosphate esters. Zero in the figure represents the wet combing force resulting from the use of water alone.

A first formulation in accordance with the present invention was prepared using CRODAFOS HCE, which is a mixture of alkoxylated phosphate esters and non-alkoxylated phosphate esters, more specifically, about 55% PEG-5 oleyl mixed with about 45% dioleyl phosphate, and Polyquaternium-10.

A second formulation in accordance with the present invention was prepared using CRODAFOS 1435 as the phosphate ester, which is about 55% PEG-10 isostearyl mixed with about 45% di-isostearyl phosphate, and Polyquanternium-10.

A third formulation in accordance with the present invention was prepared using dioleyl phosphate and Polyquaternium-10.

A fourth formulation in accordance with the present invention was prepared using isostearyl phosphate and Polyquaternium-10.

A first prior art formulation was prepared using the quaternized phosphate ester like that described in the U.S. Pat. No. 5,683,683, and Polyquaternium-10. Specifically Arlasilk (also referred to as "EFA") available from Croda which is linoleamidopropyl-PG-dimonium chloride phosphate (30% solids in $H_2O$) used with all the phosphate esters in Example 7, was used at 2% by weighted bonding on the active material.

A second prior art formulation was prepared using the alkoxylated phosphate ester like that described in U.S. Pat. No. 4,298,494, which is ethoxylated phosphate esters, and Polyquaternium-10. Specifically, CRODAFOS N3A was used, which is about 100% oleth-3-phosphate used at a level of 2% on an active basis was used.

A third prior art formulation was prepared using the alkoxylated phosphate ester like those described in U.S. Pat. No. 4,381,259, which is a mixture of ethoxylated and propoxylated phosphate esters, and Polyquaternium-10. Specifically, CRODAFOS SG, which is 100% PPG-5-ceteth-10-phosphate at 2% weight based on actives is used.

The conditioning properties of above-mentioned formulations can be compared by testing the relative reduction in combing force of these formulations using the techniques generally described in U.S. Pat. No. 6,562,328 to Pereira et al. and in particular, examples 5 and 6 thereof, the text of which is hereby incorporated by reference. This is accomplished using medium European brown virgin hair tresses (International Hair Importers, Glendale, N.Y.). The device used was a Dia-stron MTT #160. Two gram weight samples of hair, 7.5 inch lengths, which had been washed with a 5% sodium lauryl sulfate solution and rinsed were used. The hair samples are treated for a period of about a minute using about 2 mL of the test material. After about a minute, the tresses are rinsed completely in tap water and tested.

The reduction in combing force was measured by first measuring the combing force of wet hair tresses without any treatment of above-mentioned formulations using a Diastron Miniature Tensile Tester, then the hair tresses were treated with the Control formulation, the first prior art formulation, the second prior art formulation, and the first and second formulations of the present invention, respectively. Then the reduction in combing force of the hair tresses after the treatment with the aforementioned formulations was determined using Diastron Miniature Tensile Tester.

As shown in FIGS. 1 and 4, the results of the reduction in combing force tests demonstrate that the combing forces measured after the treatment with the shampoo formulation of the present invention comprising CRODAFOS HCE, CRODAFOS 1435, dioleyl phosphate, and isostearyl phosphate were about −27, −38, −35 and −15 Joules, respectively (change in total work).

On the other hand, the combing forces measured after the treatment with the first, second and third prior art formulations were about 12, 4 and −3 Joules, respectively. The first two, while better than using the polyquat alone, were still not as good as water alone. The third provided only a very small improvement. Thus, the use of the phosphate esters and polyquat mixture of the present invention resulted in vastly superior conditioning in combing force reduction when compared to the best of these prior art formulations and to water. Indeed, superior conditioning of a force reduction of greater than 10 Joules, and, in some instances, a reduction even greater than 20 Joules, was realized by use of the formulations of the invention.

FIG. 4 shows the wet combing evaluations for the four embodiments of the present invention described above along with the three aforementioned prior art formulations. Once again, each of the four embodiments of the present invention showed superior conditioning by establishing a force reduction of greater than 10 Joules, and, in some instances, a reduction of even greater than 20 Joules. Moreover, as shown by the peak load data in FIG. 4, the CRODA HCE, CRODAFOS 1435, dioleyl phosphate, and isostearyl phosphate containing formulations each provided a decrease in peak load (about −39, −47, −51, and −15 gmf, respectively) as compared with Polyquaternium-10 alone, and the CRODAFOS N3A and Arlasilk containing formulations.

Figure 2:
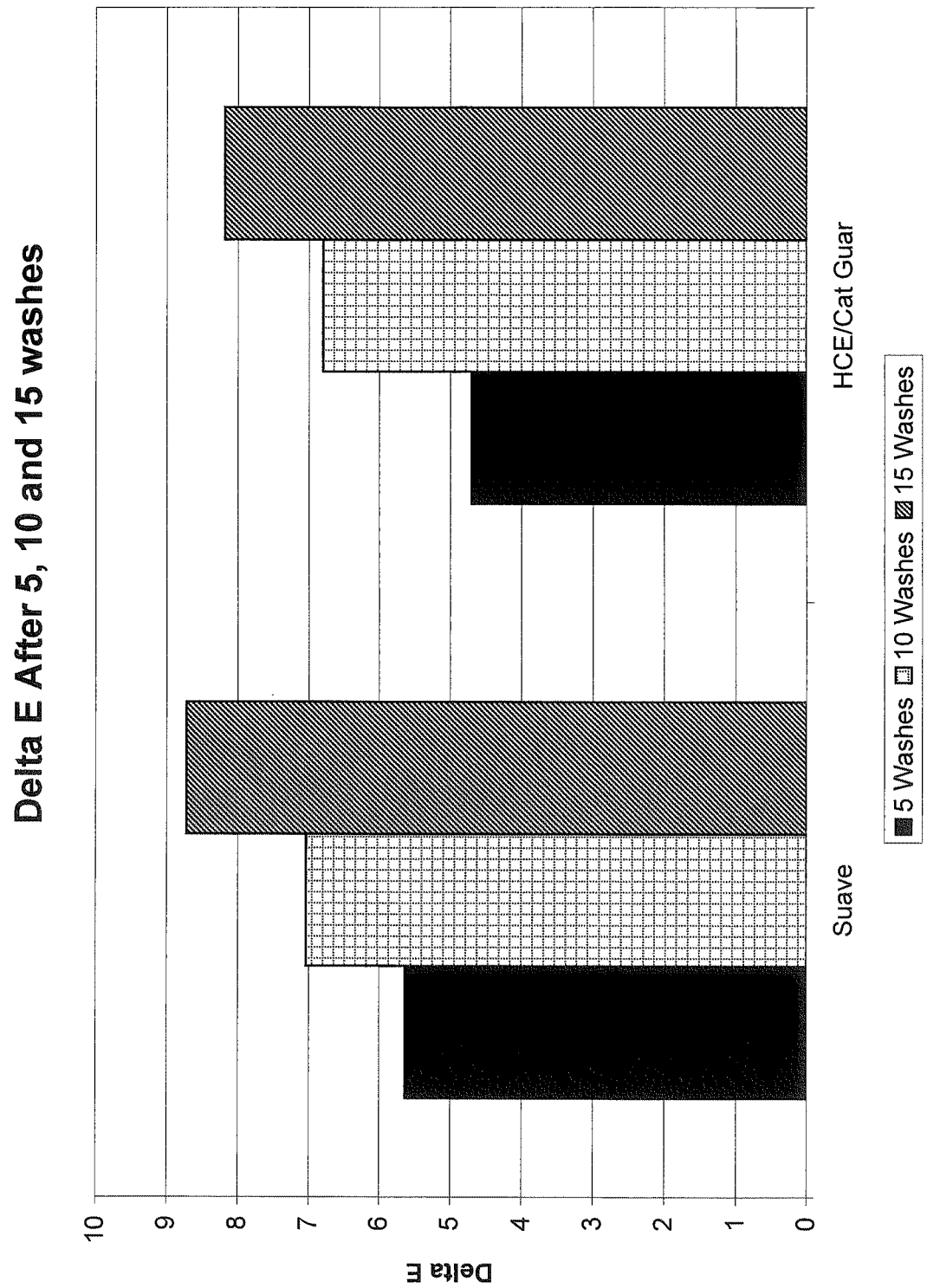
FIG. 2 represents color measurements (delta E) made using a Labscan colorimeter after 5, 10 and 15 washes reading left to right.

As shown in FIG. 2, the delta E after 5, 10 and 15 washes respectively of a commercially available shampoo (Suave) with and without the polyquats and phosphate esters of the invention were obtained. See Example 4. As shown in FIG. 2, after 5 (light gray), 10 (dark gray) and 15 (white) washes, the delta E was measured. A lower delta E was exhibited at each level for the invention (HCE/Guar) versus the same material without the invention. This is indicative of retaining additional color relative to the stock Suave shampoo.

Figure 3:
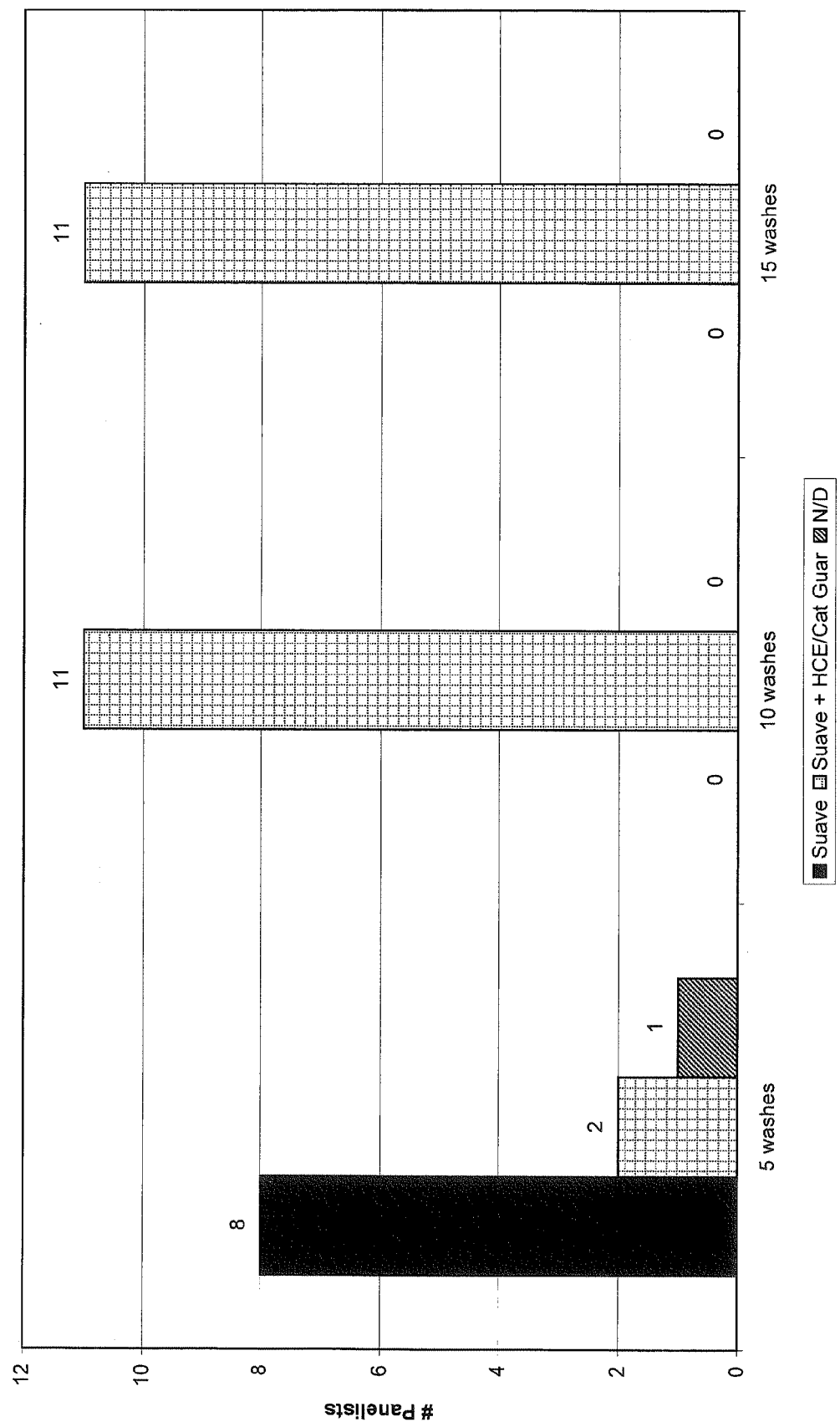
FIG. 3 represents the opinions of panelists asked to evaluate which products reduced color the least after repeated washing.

The analysis of panelists was also obtained as shown in FIG. 3, the majority of the 11 panelists (8) believed that the hair treated with Suave maintained more color after 5 washes while 2 panelists thought that Suave & HCE/Guar (polycationic guar) was darker and 1 panelist saw no difference between the samples. These are represented in the figure by light gray, dark gray and white, respectively. After 10 and 15 washes, however, all 11 panelists believed 154-2-05, the Suave with HCE/Guar, maintained more of the hair's synthetic color.

Additional Ingredients

The compositions of the invention may also include a wide range of "additional" ingredients used to make the personal care products. Some suitable miscellaneous "additional" ingredients commonly used in the cosmetic and personal care industry are described in The CTFA Cosmetic Ingredient Handbook, (2nd Ed., 1992), which is incorporated by reference herein. More specifically these personal care products and formulations of the present invention can include one or more additives such as absorbents, anti-acne agents, anti-irritants, antiperspirants, anticaking agents, antifoaming agents, antimicrobial agents, antioxidants, antidandruff agents, astringents, binders, buffers, biological additives, botanical extracts, buffering agents, bulking agents, chelating agents, chemical additives, coupling agents, conditioners, colorants, cosmetic astringents, cosmetic biocides, denaturants, drug astringents, detergents, dispersants, external analgesics, film formers, foaming agents, fragrance components, humectants, keratolytics, opacifying agents, pH adjusters, preservatives, propellants, proteins, retinoids, reducing agents, sequestrants, skin bleaching agents, skin-conditioning agents (humectants, miscellaneous, and occlusive), skin soothing agents, skin healing agents, softeners, solubilizing agents, lubricants, penetrants, plasticizers, solvents and co-solvents, sunscreening additives, salts, essential oils, and vitamins. When present, these additives are provided in an amount which is consistent with the desired use and end product.

pH Adjusters

Examples of suitable pH adjusters include sodium hydroxide, triethanolamine, and aminomethylpropanol, and mixtures thereof. If pH adjusters are present in a final product composition, the amount may vary from about 0.01% to about 5%, preferably, from about 0.1% to about 2% by weight of the composition.

Film Formers

Examples of suitable film formers include glycerin/diethylene glycol myristate copolymer, glycerin/diethylene glycol adipate copolymer, ethyl ester of PVM/MA copolymer, PVP/dimethiconylacrylate/polycarbamyl/polyglycol ester, and mixtures thereof. If the film formers are present in the final product compositions, the amount may vary from about 0.1% to about 15.0% by weight of the composition, preferably, from about 0.1% to about 2.5% by weight of the composition.

Vitamins

Examples of suitable vitamins include ascorbic acid, tocopherol, tocopherol acetate, retinoic acid, retinol, and retinoids.

Conditioning Agents

The personal care products of the present invention may be conditioners and or conditioning shampoos body washes, cleansers, hair colors and/or hair relaxers which may include hydrolyzed animal protein as additional conditioning agents. Croda Incorporated sells an example of a commercially available material under the trade name Crotein Q™. Other examples include urea, glycerol, and propoxylated glycerols, including those described in U.S. Pat. No. 4,976,953, which is incorporated by reference herein.

Surfactants

In addition to the compositions of the invention, and particularly when used in connection with shampoos, surfactants, and in particular, surfactants that will not strip color, may be present in the compositions of the invention. These may include, without limitation, one or more nonionic surfactants, anionic surfactants, cationic surfactants, amphoteric surfactants, zwitterionic surfactants, and mixtures thereof. For some of surfactants that may be used in combination with the compositions of the invention, please see McCutcheon's, Detergents and Emulsifiers, (1986), U.S. Pat. Nos. 5,151,210, 5,151,209, 5,120,532, 5,011,681, 4,788,006, 4,741,855, U.S. Pat. Nos. 4,704,272, 4,557,853, 4,421,769, 3,755,560; all incorporated herein by reference in their entirety.

Emulsifiers

The compositions of the invention may also include various emulsifiers. In the final product compositions of the invention, emulsifiers may be included in the amount of up to about 10%, preferably, in the amount of from about 0.5% to about 5% by weight of the composition. The examples of suitable emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, polyethyleneglycols, polypropyleneglyocis, and mixtures thereof.

Thickeners

The compositions of the invention may also include various thickeners, such as cross-linked acrylates, nonionic polyacrylamides, xanthan gum, guar gum, gellan gum, and the like; polyalkyl siloxanes, polyaryl siloxanes, and aminosilicones. In the final product compositions of the invention, thickeners may be included in the amount of up to about 10%, preferably, in the amount of from about 0.2% to about 5% by weight of the composition. The specific examples of the suitable thickening silicon compounds include polydimethylsiloxane, phenylsilicone, polydiethylsiloxane, and polymethylphenylsiloxane. Some of the suitable silicon compounds are described in European Patent Application EP 95,238 and U.S. Pat. No. 4,185,017, which are incorporated herein by reference. The compositions of the invention may also include silicone polymer materials, which provide both style retention and conditioning benefits to the hair. Such materials are described in U.S. Pat. No. 4,902,499, which is incorporated herein by reference.

Colorants

Hair color examples can be found in patents such as U.S. Pat. No. 4,865,618 (Junino et al.). Without setting any limitations, as an example, the invention herein can be incorporated into any of the application examples disclosed by Junino et al. starting in column 22. Simply one skilled in the art can just add the, for example, about 3% w/w Crodafos HCE and 0.5% w/w Optasence CP-6 (Polyquaternium 6) to any of the application examples described by Junino et al. As is known to those familiar with the art, hair color (tint) formulations contain various dyes, couplers etc. as also described in Junino et al. in U.S. Pat. No. 4,865,618, which is hereby incorporated by reference.

EXAMPLES

Example 1

Formulation

| AB6-55 | |
| --- | --- |
| Deionized Water | qs |
| ALES (25% active) | 56.00 (14% AM) |
| ALS (28% active) | 14.28 (4% AM) |
| Incronam 30 | 8.66 (2.6% AM) |
| Phosphate ester* | 2.0% based on active matter |
| Polymer JR-30M | 0.5 |
| Neolone 950 | 0.1 |

*except control

Procedures to prepare shampoo prototypes are the same for each batch. Specifically, the vessel was charged with water and agitation started. The polymer (Polymer JR-30M) was then sifted in while mixing and mixing was continued until the polymer was completely dissolved in water. Incronam 30, ammonium laureth-2 sulfate solution (ALES), and ammonium lauryl sulfate solution (ALS) were then added while mixing. The phosphate esters were then added along with any additional ingredients.

These formulations, whose testing is reflected in FIGS. 1 and 4, were prepared in accordance with this example. Except the control, which contained no phosphate esters, the others all included equal levels of phosphate esters. All were used at 2% on an actives basis. The phosphate ester materials used, as described previously, were dioeyl phosphate, isostearyl phosphate, Arlasilk EFA, CRODAFOS N3A, CRODAFOS SG, CRODAFOS HCE and CRODAFOS 1435.

Example 2

Experimental Wet Combing Evaluation of the Formulation of Example 1

Results:

| Shampoo Formulation | change in peak load (gmf) | change in total work (Joules) |
| --- | --- | --- |
| PQ-10 | 34 | 59 |
| Arlasik EFA/PQ-10 | −11.53 | 11.76 |
| Crodafos NA3/PQ-10 | 3.4 | 4.1 |
| Crodafos SG/PQ-10 | −22.78 | −2.95 |
| Crodafos HCE/PQ-10 | −39.41 | −27.41 |
| Crodafos 1435/PQ-10 | −47.08 | −38.46 |
| Dioleyl Phosphate/PQ-10 | −51.6 | −35.85 |
| Isostearyl Phosphate/PQ-10 | −15.22 | −15.33 |

The shampoo containing CRODAFOS HCE or Crodafos 1435 and polyquat showed outstanding detangling (decrease in peak load) and overall conditioning (decrease in total work).

Similarly, the formulations containing dioleyl phosphate/PQ-10 or isostearyl phosphate/PQ-10 showed improved detangling (decrease in peak load) and overall conditioning (decrease in total work). The performance of the dioleyl phosphate/PQ-10 containing formulation showed improved detangling (decrease in peak load) and overall conditioning (decrease in total work) compared to Crodafos NA3/PQ-10, Crodafos SG/PQ-10, Crodafos HCE/PQ, confirming the phosphate ester/PQ-10 synergism.

Example 3

Hair Relaxer Composition

| | Material | % |
| --- | --- | --- |
| Part A | KERALENIS (Dicetyl Phosphate (and) Ceteth-10 Phosphate (and) Cetearyl Alcohol (and) Cetyl Alcohol (and) PPG-5 Ceteth-20)(about 18% of phosphate esters by weight) | 13.00 |
| | Mineral Oil | 15.00 |
| | Petrolatum | 21.00 |
| Part B | Deionized Water | 37.90 |
| | Optasense CP6 (40 weight % of Polyquaternium-6) | 1.00 |
| | Propylene Glycol | 2.00 |
| Part C | Deionized Water | 6.00 |
| | Sodium Hydroxide Pellets, 97% | 2.10 |
| Part D | KERAVIS (Hydrolyzed Vegetable Protein PG-Propyl Silanetriol) | 1.00 |
| | CROPEPTIDE W (Hydrolyzed Wheat Protein (and) Hydrolyzed Wheat Starch) | 1.00 |
| | TOTAL | 100.00 |

All ingredients of Part A were heated to 65-70° C. in one vessel with mixing. A separate vessel was charged with water and Optasense CP6 was added and mixed until completely dissolved. Propylene Glycol was then added and heated with the ingredients of Part B to 65° C.-70° C. with mixing. When both Part A and Part B were between 65° C.-70° C., Part B was slowly added to Part A with vigorous mixing until the mixture was uniform. The mixture was then moved to a side sweep mixer, and cooled to 50° C. At 50° C., the mixture was set in a water bath and cooled to 40° C. The ingredients of Part C were then combined in a separate vessel with mixing, and cooled to room temperature. When the main batch was at 40° C., Part C was slowly added to the A & B mixture with continued mixing until completely smooth and homogeneous. Part D was then added to the A, B & C mixture.

Example 4

Hair Color Protection Shampoo: Crodafos HCE & Polymer Evaluation For Color Protection in a Shampoo Suave Daily Clarifying Shampoo sold by Unilever was used in this evaluation. 2% Crodafos HCE and 0.5% active Aquacat CG518 (Guar) from Hercules were added to the Suave Daily Clarifying Shampoo (sample formula 154-2-05), pH was adjusted to 5.71 after addition using NaOH solution.

Eight 1.5 cm thick hair tresses were used (hair was labeled Normal Bleached Hair). The hair tresses were dyed with L'Oreal Superior Preference 5 MB Medium Auburn Hair Dye according to the manufacturers instructions.

Hair tresses treated with the hair color were then washed with 1 mL of shampoo and rinsed for 30 seconds per wash.

Hair was treated with L'Oreal kit conditioner for 2 minutes and rinsed for 30 seconds.

The total change in color (ΔE) was determined using a Hunter LabScan Colorimeter as described previously and the results are illustrated in FIG. 2. The panel analysis also was conducted using the hair treated in accordance with this example. See FIG. 3.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of imparting superior conditioning to hair comprising applying a personal care product to hair, the personal care product comprising:
(a) a polyquaternium compound having 100 or more quaternary nitrogen groups and having a weight average molecular weight of between 30,000 and 1,000,000;
(b) at least one nonalkoxylated phosphate ester of fatty alcohols, wherein said nonalkoxylated phosphate ester is selected from the group consisting of dioleyl phosphate ester, monocetyl phosphate ester, and isostearyl phosphate ester, wherein a ratio of said nonalkoxylated phosphate ester to said polyquaternium compound is at least about 2:1 and wherein a total amount of said nonalkoxylated phosphate ester and said polyquaternium compound ranges from between about 0.5% and about 5% by weight of said personal care product, and
(c) an additional ingredient,
wherein said personal care product is capable of reducing a wet combing force of a hair sample treated therewith by at least about 10 Joules relative to water, and
wherein the personal care product does not contain an alkoxylated phosphate ester.

2. The method of claim 1, wherein said personal care product is capable of reducing a wet combing force of a hair sample treated therewith by at least about 20 Joules relative to water.

3. The method of claim 1, wherein a color change of said hair after about fifteen washes is reduced relative to a same product without said nonalkoxylated phosphate ester and said polyquaternium compound.

4. The method of claim 1, wherein said nonalkoxylated phosphate ester is a mixture of a nonalkoxylated monophosphate ester and a nonalkoxylated diphosphate ester, wherein an amount of said nonalkoxylated diphosphate ester is greater than an amount of said nonalkoxylated monophosphate ester.

5. The method of claim 1, wherein said personal care product is a hair color and wherein a ratio of said nonalkoxylated phosphate ester to said polyquaternium compound is at least about 4:1.

6. A method of preserving the degree of hair color in synthetically colored hair comprising applying a personal care product to hair, the personal care product comprising:
(a) a polyquaternium compound having 100 or more quaternary nitrogen groups and having a weight average molecular weight of between 30,000 and 1,000,000;
(b) at least one nonalkoxylated phosphate ester of fatty alcohols, wherein said nonalkoxylated phosphate ester is selected from the group consisting of dioleyl phosphate ester, monocetyl phosphate ester, and isostearyl phosphate ester, wherein a ratio of said nonalkoxylated phosphate ester to said polyquaternium compound is at least about 2:1 and wherein a total amount of said nonalkoxlyated phosphate ester and said polyquaternium compound ranges from between about 0.5% and about 5% by weight of said personal care product, and
(c) an additional ingredient,
wherein said personal care product is capable of reducing a wet combing force of a hair sample treated therewith by at least about 10 Joules relative to water, and
wherein the personal care product does not contain alkoxylated phosphate ester.

7. The method of claim 6, wherein the color change of said hair after about fifteen washes is reduced relative to a same product without said nonalkoxylated phosphate ester and said polyquatenium compound.

8. The method of claim 6, wherein said nonalkoxylated phosphate ester is a mixture of nonalkoxylated monophosphate ester and nonalkoxylated diphosphate ester, where an amount of said nonalkoxylated diphosphate ester is greater than an amount of said nonalkoxylated monophosphate ester.

9. The method of claim 6, wherein said personal care product is a hair color and wherein a ratio of said nonalkoxylated phosphate ester to said polyquaternium compound is at least about 4:1.

10. A method of imparting superior conditioning to hair comprising applying a personal care product to hair, the personal care product comprising:
(a) a polyquaternium compound having 100 or more quaternary nitrogen groups and having a weight average molecular weight of between 30,000 and 1,000,000;
(b) at least one nonalkoxylated phosphate ester of fatty alcohols wherein said nonalkoxylated phosphate ester has a fatty alcohol based group having a chain length of between about $C_8$ and about $C_{22}$, wherein a ratio of said nonalkoxylated phosphate ester to said polyquaternium compound is at least about 2:1 and wherein a total amount of said nonalkoxylated phosphate ester ranges from about 0.15% and about 2% by weight of said personal care product, and (c) an additional ingredient, wherein said personal care product is capable of reducing a wet combing force of a hair sample treated therewith by at least about 10 Joules relative to water, and wherein the personal care product does not contain alkoxylated phosphate ester.

11. The method of claim 10, wherein said personal care product is capable of reducing a wet combing force of a hair sample treated therewith by at least about 20 Joules relative to water.

12. The method of claim 10, wherein a color change of said hair after about fifteen washes is reduced relative to a same product without said nonalkoxylated phosphate ester and said polyquaternium compound.

13. The method of claim 10, wherein said nonalkoxylated phosphate ester is a mixture of a nonalkoxylated monophosphate ester and a nonalkoxylated diphosphate ester, wherein an amount of said nonalkoxylated diphosphate ester is greater than an amount of said nonalkoxylated monophosphate ester.

14. The method of claim 10, wherein said personal care product is a hair color and wherein a ratio of said nonalkoxylated phosphate ester to said polyquaternium compound is at least about 4:1.

15. A method of preserving the degree of hair color in synthetically colored hair comprising applying a personal care product to hair, the personal care product comprises:

(a) a polyquaternium compound having 100 or more quaternary nitrogen groups and having a weight average molecular weight of between 30,000 and 1,000,000;

(b) at least one nonalkoxylated phosphate ester of fatty alcohols wherein said nonalkoxylated phosphate ester has a fatty alcohol based group having a chain length of between about $C_8$ and about $C_{22}$, wherein a ratio of said phosphate ester to said polyquaternium compound is at least about 2:1 and wherein a total amount of said nonalkoxylated phosphate ester ranges from about 0.15% and about 2% by weight of said personal care product, and (c) an additional ingredient, wherein said personal care product is capable of reducing a wet combing force of a hair sample treated therewith by at least about 10 Joules relative to water, and wherein the personal care product does not contain alkoxylated phosphate ester.

16. The method of claim 15, wherein the color change of said hair after about fifteen washes is reduced relative to a same product without said nonalkoxylated phosphate ester and said polyquatenium compound.

17. The method of claim 15, wherein said nonalkoxylated phosphate ester is a mixture of a nonalkoxylated monophosphate ester and a nonalkoxylated diphosphate ester, where an amount of said nonalkoxylated diphosphate ester is greater than an amount of said nonalkoxylated monophosphate ester.

18. The method of claim 15, wherein said personal care product is a hair color and wherein a ratio of said nonalkoxylated phosphate ester to said polyquaternium compound is at least about 4:1.

* * * * *